United States Patent [19]

Shanbrom

[11] Patent Number: 5,545,401
[45] Date of Patent: Aug. 13, 1996

[54] ANTIVIRAL, SPERMICIDAL VAGINAL GEL AND FOAM CONTAINING LOW MOLECULAR WEIGHT POVIDONE-IODINE

[76] Inventor: Edward Shanbrom, 2252 Liane La., Santa Ana, Calif. 92705

[21] Appl. No.: 254,025

[22] Filed: Jun. 2, 1994

[51] Int. Cl.⁶ .......................... A61K 31/79; A61K 33/18
[52] U.S. Cl. .................. 424/78.07; 424/430; 424/431; 424/432; 424/433; 424/667; 424/669; 514/772.1; 514/966; 514/967; 604/55
[58] Field of Search ................... 424/430, 667, 424/431, 669, 432, 433, 78.07; 514/966, 967, 772.1; 604/55

[56] References Cited

U.S. PATENT DOCUMENTS

| | | | |
|---|---|---|---|
| 2,739,922 | 3/1952 | Shelanski | 167/70 |
| 2,975,099 | 3/1961 | Goyan et al. | 167/64 |
| 3,234,091 | 2/1966 | Lang et al. | 167/64 |
| 4,755,378 | 7/1988 | Buxton et al. | 424/80 |

*Primary Examiner*—Frederick Krass
*Attorney, Agent, or Firm*—Price, Gess & Ubell

[57] ABSTRACT

A virucidal, spermicidal vaginal gel consisting essentially of povidone iodine having a povidone to iodine ratio of about 15:1 or higher containing from about one percent to about twenty percent low molecular weight povidone having a molecular weight of about 20 kd or lower, the gel having a viscosity such that a conical body drawn from a body of the same does not visibly slump at 37C. for a period of at least one minute and a method of preventing sexual transmission of disease and preventing pregnancy using the same are disclosed.

4 Claims, No Drawings

ANTIVIRAL, SPERMICIDAL VAGINAL GEL AND FOAM CONTAINING LOW MOLECULAR WEIGHT POVIDONE-IODINE

BACKGROUND OF THE INVENTION

This invention relates to the treatment of and the prevention of vaginal infections and the prevention of transmission of sexually transmitted diseases. The methods of this invention may be used to kill or inactivate virus, bacteria, chlamydia, rickettsia, mycoplasma and other potentially pathogenic microorganisms in humans and other mammals.

The following abbreviations used in the following disclosure are defined as follows:

| | |
|---|---|
| Povidone | Povidone USP and equivalent products. Povidone has a molecular weight of above about 30 kd, the average molecular weight being about 40 kd typically. Povidone is polyvinyl pyrrolidone of the type generally available from GAF and BASF. |
| Povidone iodine | Povidone complexed with iodine. Povidone iodine typically comprises about 5 weight percent of iodine, plus about 10 weight percent iodide. |
| LMW Povidone | Polyvinyl pyrrolidone that has an average molecular weight of about 15,000 kd, typically 15,000 to 25,000 kd. |

Povidone-iodine is a widely used commercial product. Povidone-iodine, abbreviated here as povidone iodine is a complex of molecular iodine with polyvinyl pyrrolidone. Povidone iodine complexes of the type under consideration have been described in the literature and are marketed by The Purdue-Frederick Co. When percent concentrations are referred to in connection with povidone iodine, the percentage refers to the percent of povidone iodine by weight, based upon the weight of the solution or material to which the povidone iodine is added. Thus, a 1 weight percent ($^w$/o) solution of povidone iodine indicates that enough povidone iodine has been dissolved to result in a concentration of 1 $^w$/o povidone iodine. In most instances, povidone iodine is added as a solution, e.g. 10% solution in water, pH about 1.5, but it can be added as a powder or otherwise. Povidone iodine powder contains approximately 85% povidone, 10% I and 5% iodide. A 10% solution of this powder contains 1% free, available iodine. (Gershenfeld, Am. J. Surgery 94, 938 (1957)).

Many and diverse diseases are transmitted sexually. Among the more common sexually transmitted diseases are condylomata acuminata (venereal warts), gonorrhea, syphilis, herpes simplex, granuloma venereum, chancroid, granuloma inguinale, non-gonococcal urethritis, acute pelvic inflammatory disease, vaginitis, and anorectal disease, and, of increasing concern, AIDS. Commonly sexually transmitted disease-causing organisms include *Neisseria gonorrhoeae, Chlamydia trachomatis,* Papillomavirus, *Ureaplasma urealyticum, Mycoplasma hominis, Trichomonas vaginalis* and Candida species.

Condylomata acuminata (venereal warts) is a sexually transmitted disease which has increased markedly in both adults and children during the past 15 years. The human papilloma virus is notoriously difficult to treat and often requires multiple office visits utilizing a variety of treatment modalities. Venereal warts are an ancient disease, but the relationship between certain human papillomavirus serotypes and genital neoplasia is just being recognized. Women are at higher risk for development of neoplasia from the infection and are more likely to be reinfected, because a male partner's lesions may be invisible without application of acetic acid or examination of a urethral smear. Other factors that favor progression to cancer are young age at first exposure, multiplicity of exposures, and immunosuppression.

Nonoxynol-9, a detergent that is widely used as a spermicide, has limited antibiotic activity; however, it does not kill or inactivate papillomavirus, the causative organism for venereal warts.

Vaginitis is a wide-spread disease which may be transmitted sexually or through other means. Vaginitis is a manifestation of a local infection by *T. vaginalis,* Candida, or *Gardnerella vaginalis* or other organisms. This invention has application to the treatment of vaginal diseases whether sexually transmitted or acquired through other contacts.

Herpesviruses, of which CMV is a member, represent a very large group of viruses which are responsible for, or involved in, cold sores, shingles, a venereal disease, mononucleosis, eye infections, birth defects and probably several cancers. Three subfamilies are of particular importance. The alpha subfamily includes HSV 1 (herpes simplex virus 1) which causes cold sores, fever blisters, eye and brain infections, HSV 2 (herpes simplex virus 2) which cause genital ulceration, and HSV 3 (HSV varicella zoster) which causes chicken pox, shingles and brain infections. The beta subfamily includes HSV 5, the principal member of which is CMV discussed above. The gamma subfamily includes HSV 4 (Epstein-Barr) which cause infectious mononucleosis and is involved in Burkitt's lymphoma and nasopharyngeal carcinoma.

The use of elemental iodine as an antiseptic dates back to about 1839. It is used today for various medicinal purposes. The combination of iodine with various solubilizing polymers led to a class of new compositions known as iodophors, which dominate the market once satisfied by simple alcoholic or aqueous iodine solutions. The iodine complexes with either nonionic surfactants, eg, polyethylene glycol mono(nonylphenyl)ether, or poly(vinylpyrrolidone) (povidone). The complexes function by rapidly liberating free iodine in water solutions. They exhibit good activity against bacteria, molds, yeasts, protozoa, and many viruses; indeed, of all antiseptic preparations suitable for direct use on humans and animals and upon tissues, only povidone iodine is capable of killing all classes of pathogens: gram-positive and gram-negative bacteria, mycobacteria, fungi, yeasts, viruses and protozoa. Most bacteria are killed within 15 to 30 seconds of contact. These iodophors are generally non-toxic, nonirritating to the skin and nonirritating upon short term application to membranes, non-sensitizing, and non-corrosive to most metals (except silver and iron alloys). Medicinal povidone iodine preparations include aerosol sprays, gauze pads, lubricating gels, creams, solutions, douche preparations, suppositories, gargles, perineal wash solutions, shampoos, and skin cleansers and scrubs. Povidone iodine preparation are applied topically to the skin and to membranes, e.g. vaginal membranes, and in infected wounds and surgical incisions. The uses continue to be largely medicinal, though some iodophors are used in industrial sanitation and disinfection in hospitals, building maintenance, and food-processing operations. There has been some interest in the use of iodine for purification of potable water and swimming pools. Two other iodine-containing compounds, p-tolyl diiodomethyl sulfone and p-chlorophenyldiiodomethyl sulfone have been recommended as preservatives.

Iodine and iodine-containing compounds and preparations are employed extensively in medicine, eg, as antiseptics, as drugs administered in different combinations in the prophylaxis and treatment of certain diseases, and as therapeutic agents in various thyroid dyscrasias and other abnormalities. Iodine is a highly reactive substance combining with proteins partly by chemical reaction and partly by adsorption. Therefore its antimicrobial action is subject to substantial impairment in the presence of organic matter such as serum, blood, urine, milk, etc. However, where there is no such interference, non-selective microbicidal action is intense and rapid. A saturated aqueous solution of iodine exhibits anti-bacterial properties. However, owing to the low solubility of iodine in water (33 mg/100 ml at 25° C.), reaction with bacteria or with extraneous organic matter rapidly depletes the solution of its active content. Iodide ion is often added to increase solubility of iodine in water. This increase takes place by the formation of triiodide, $I_2+I^-=I_3^-$. An aqueous solution of iodine and iodide at a pH of less than 8 contains mainly free diatomic iodine $I_2$ and the triiodide $I_3^-$ The ratio of I and $I^-$ depends upon the concentration of iodide.

An important solubilizing agent and carrier for iodine is polyvinyl pyrrolidone (povidone), one grade of which is identified as povidone USP. Povidone iodine, is widely used externally on humans as an antiseptic. Such products are marketed as Betadine and Isodine, povidone iodine products and the preparation of such products are described in U.S. Pat. Nos. 2,707,701, 2,826,532, and 2,900,305 to Hosmer and Siggia, assigned to GAF Corporation and in a number of GAF Corporation publications; see, e.g. Tableting with Povidone USP (1981) and Povidone Polyvinylpyrrolidone (1982). Povidone iodine powder contains approximately 85% povidone, 10% I and 5% Iodide. A 10% solution of this powder contains 1% free, available iodine. (Gershenfeld, Am. J. Surgery 94, 938 (1957)).

Under ordinary conditions, povidone is stable as a solid and in solution. The single most attractive property of povidone is its binding capability. This property has permitted utilization in numerous commercial applications. Small quantities of povidone stabilize aqueous emulsions and suspensions, apparently by its absorption as a thin layer on the surface of individual colloidal particles. The single most widely studied and best characterized povidone complex is that of povidone-iodine. For example, hydrogen triiodide forms a complex with povidone that is so stable that there is no appreciable vapor pressure. It is superior to tincture of iodine as a germicide.

The use of conventional povidone iodine, i.e. compositions which have an povidone to iodine ratio of under 10 to 1, typically 8.5 to 1, in vaginal treatments has been reported. Women being prepared for total abdominal hysterectomy were treated by insertion of povidone-iodine tampons that remained in the vagina until the end of the operation. Statistically significant decreases both in infectious morbidity and in the percentage of positive cultures from the cervix and vagina, at the time of the operation resulted from this use of povidone-iodine. Vaginal Preparation with Povidone-Iodine before Abdominal Hysterectomy, Zakut Z; Lotan M; Bracha Y, Clin Exp Obstet Gynecol 14 (1). 1987. 1–5. The use of povidone-iodine ('Betadine') pessaries in the treatment of candidal and trichomonal vaginitis was reported by Henderson JN; Tait IB Curr Med Res Opin 1975, 3 (3) p157–62. In the Henderson et al study one hundred and thirty-five women suffering from trichomonal, candidal, or both infections simultaneously, were treated with povidone-iodine pessaries, 2 pessaries being inserted nightly. Ninety-nine women were given a 7-day course of treatment, but the results obtained were disappointing, and the authors do not recommend such a regime for routine treatment. Better results were obtained with the recommended 14-day course. A further 36 women suffering from chronic trichomonal and/or candidal infections which had previously resisted orthodox treatment were given a prolonged 28-day course of pessary treatment. The results obtained were very encouraging, 92% of the trichomonal and 96% of the candidal infections being cured. Furthermore, although povidone-iodine is slightly less effective in trichomoniasis, most patients suffering from a chronic infection (candidal, as well as trichomonal) were cured by the one preparation. Side-effects did occur. Subjective symptoms, especially any offensive odor, disappeared within 3 days of the start of the treatment. The authors recommend that the 28-day course of povidone-iodine pessaries is used in those cases where trichomoniasis or candidiasis has been a therapeutic problem in the past, particularly if the patient is currently on the oral contraceptive pill.

Other uses of povidone iodine in vaginal preparations and as a spermicidal preparations have been reported. The treatment of minor vaginal irritation with disposable povidone iodine preparation (Betadine Medicated Douche) in cases associated with infertility was reported by Beaton J H, et al, Int J Fertil 29 (2). 1984. 109–112. The effect of chemical intravaginal contraceptives and betadine on ureaplasma urealyticum was studied by Amortegui, A. J.; Melder, R. J.; Meyer, M. P.; Singh, B., CONTRACEPTION; 30(2), pp. 135–142 1984. The purpose of the study was to find a barrier contraceptive agent capable of controlling infections and sexual transmission of Ureaplasma urealyticum from the female genital tract, especially to help reduce non-gonococcal urethritis in males caused by this organism. In vitro antimicrobial activity of Betadine(TM-Purdue Frederick Co.) against the eight serotypes of the organism was investigated. The results indicate that some of these contraceptives produce partial inhibition of the Ureaplasma at low dilutions, while Betadine produces a ureaplasmicidal effect up to dilutions of 1:64. Quantitative studies of the interaction of polyvinylpyrrolidone iodine and spermatozoa were conducted by Pfannschmidt N; Nissen HP, Z Hautkr Nov. 15, 1988. In this study, 27 ejaculates were incubated together with polyvinyl pyrrolidone iodine diluted with physiological saline solution in various proportions. 10 minutes, 1 hour, 4 hours, and 20 hours later, we determined the percentages of mobile and viable spermatozoa in both the native and the incubated seminal fluid. 1% polyvinyl pyrrolidone iodine solution was totally spermicidal already after 10 minutes of incubation. 0.1% solution only slightly reduced the sperm motility and viability. 0.01% polyvinyl pyrrolidone iodine solution even resulted in a temporary increase of motility.

Douche preparations containing povidone iodine are widely used, and efforts have been made to treat and/or prevent vaginal infections with povidone iodine.

Notwithstanding considerable interest in povidone iodine-based spermicide-microbicides, no satisfactory product has been developed and frequent regular use of povidone iodine products frequently results in irritation of the vaginal membrane and considerable discomfort to the user. It also is evident that no effective physical form of povidone iodine for use as a spermicide-biocide has been available. The invention described hereinafter solves the problems, both recognized and unrecognized, that have plagued workers in this field.

SUMMARY OF THE INVENTION

Gels and foaming gels containing levels of iodine in the general range of about 1 to 5 weight percent and having a ratio of povidone to I very much higher than previously disclosed, a portion of the extra povidone being low molecular weight compound for use as spermicide-biocides are disclosed.

DESCRIPTION OF THE PREFERRED EMBODIMENTS

My studies on the effect of higher than normal povidone to iodine ratios on cells and tissues of several times have established that increasing the povidone to iodine ratio very substantially above the ratio found in previous formulations, i.e. to provide at least about a 50% higher povidone to iodine ratio, of at least about 15 parts by weight of povidone to 1 part by weight of iodine, and preferable at a ratio of above 20 parts povidone to 1 part of povidone, very significantly reduce detrimental effects on cells and tissues and irritation of membranes such as the vaginal membrane. This result has been shown even in relation to highly fragile cell membranes. For example, it has been found that high povidone to iodine ratios virtually eliminate lysis of cells.

It has also been discovered that polyvinyl pyrrolidone alone is capable of killing about 2 to 5 logs of virus in body fluids; consequently, the increase in povidone to iodine ratio is not a simple dilution of the biocidal value of iodine.

Efforts to formulate an effective spermicidal gel using conventional povidone iodine, MW>~30,000 d, resulted in compositions that were either too fluid to retain any physical configuration for a period long enough to form a physical barrier to the entry of sperm into the uterus or so firm as to break too easily thereby opening cracks and passages through which the sperm may bypass the gel entirely.

It was also found that gels such as described above provided little if any lubricity and, indeed, generally tended to be so liquid as to be useless or so firm as to be likely to break into pieces which would be uncomfortable.

The compositions of this invention perform three very important functions:

First, the compositions formed an effective, retentive film, and which provide additional lubricity.

Second, the compositions were non-irritating.

Third, the compositions form gels and foams that would retain whatever physical configuration into which they were formed for a period of several minutes with only modest flow at body temperature and yet would flow when subjected to force without fragmenting.

The inclusion of low molecular weight povidone i.e. povidone having a molecular weight at least as low as 20 kd (LMW povidone) results in a compositions which have very high high-lubricity form a coherent film that entraps sperm mid semen totally eliminates or very greatly reduces the tendency of iodine to irritate the vaginal membrane.

The composition may be applied as a gel into the vagina as a lubricant, spermicide and virucide. In addition, the gel may contain a foaming agent such as pentane or, less desirably one of the chlorofluorocarbons, and contained under modest pressure until use. When applied the gel foams to partially fill the vagina.

Viscosity is widely used and widely misunderstood term. Viscosity standards within a given system when measured in the same manner may provide very precise indicia of molecular weights, stiffness, etc. However, no single system of viscosity measurements has been standardized so as to permit a precise definition of viscosity relationships in all systems. Accordingly, the best and most informative definition of the viscosity of the gels and foamed gels of this invention requires reference to observable characteristics. With these limitations in the language of the art and the uncertainty of viscosity relationships, the viscosity of the gels and foamed gels of this invention is described as follows.

Gels and foamed gels must be sufficiently firm that a cone of gel or foamed gel formed by drawing a glass stirring rod upwardly from a body of the same will hot visible slump at temperatures of between 37° C. for a period of at least 1 minute.

It will be appreciated that there are a very large number of formulations of the components as discussed that will result in a suitable vaginally protective gel or foamed gel lubricant, virucide and spermicide. The following examples are, therefore, merely illustrative and not limiting.

EXAMPLE I

Basic Formulation No. I

A gel is formulated of 5 parts LMW povidone, 5 parts of conventional povidone (MW from about 30 Kda to 50 Kda) and 10 parts of povidone iodine (povidone from about 30 Kda to 50 Kda) The above are solid powdered products. The powders are mixed and purified water is slowly added while stirring until a very thick gel is formed. This is a basic gel formulation which may completed using various constituents. This basic gel formulation is referred to hereinafter as Formula I. The povidone to iodine ratio in Formula I is about 20:1 and the iodine content is about 5 wt/% of the total solids. Forming a gel with an equal amount of water results in a 2.5 wt/% iodine content based on the total composition. The amount of water required will vary some from batch to batch depending upon the molecular weight of the povidone, which varies from lot to lot and batch to batch.

While povidone to iodine ratios of as low as about 15:1 and even slightly lower may be used, there is an increasing risk of membrane irritation if the povidone to iodine ratio is lower than about 15:1 to 17:1. The LMW povidone constitutes about 25 weight percent of the total povidone and povidone iodine. Amounts as low as about 1 weight percent as high as about 25 weight percent provide generally satisfactory lubricity and film forming characteristics. Higher amounts result in a sticky, adherent material but which lacks sufficient body to be an effective sperm barrier.

EXAMPLE II

Water is slowly to Formula I. Viscosity measurements are made periodically. Once a gel of acceptable viscosity is obtained, then any of the generally used rotating disk or cup viscometers may be used. However, a simple and effective viscosity measurement is a cone-slump measurement. Since the gel must not slump or flow over an extended period of time, the simple cone-slump test described above is satisfactory for laboratory work but a more standard production viscometer may be used in the manufacture of larger lots. Water is added slowly in increments to achieve a gel that can be pumped and extruded and which also has the specified viscosity.

EXAMPLE III

The process of Example II is followed except that the mixing is carried out at ambient laboratory temperature, or higher, in a closed pressure container filled with >1 atmosphere, preferably >3 atmospheres, of pentane. The mixing is continued until the gel is saturated with pentane.

Samples are viscosity tested in the same manner, except that when the cone is filled the gel foams and expands. The viscosity test is carried out with the cone filled with the foamed gel.

Gels may be packaged in insertable robes as are commonly used to introduce gels, creams, etc. into the vagina. A body of gel conforming to the vagina and covering the external uterine opening is formed. Some gel may enter the cervix of the uterus. During coitus the body of gel is, of course, disturbed but in most instances will prevent direct ejaculation of semen into the uterus and will quickly absorb the semen and immobilize the sperm. The reaction of iodine is quite rapid, even in low proportions in the Povidone iodine gel and the sperm will be killed before they have the opportunity to migrate to the uterus. In addition, and very importantly, the semen is very quickly incorporated into the very hygroscopic gel thereby preventing direct contact of the semen and the microbes carried therein with the vaginal membrane. The microbes, e.g. HIV, are killed virtually instantaneously and no infection results.

The user should be instructed to withdraw the insertion tube in such a manner as to form a layer of the gel, or foam, on the walls of the vagina. The gel deposited in the vagina can be manually spread over the internal vaginal walls and labia and vestibule to provide protection from microbes that may be carried on the surface or under the foreskin of the penis of the users partner in coitus.

While other forms of iodine could, in theory, be used to prevent the transmission of disease during sexual intercourse, none are suitable either because they are unduly irritating or because they do not reside on the membranes long enough and in a form that will intercept microbes carried on the penis or in the ejaculate.

It is noted in closing that the gel or foam may be left in the vagina for an extended period without discomfort or irritation of the vaginal membrane. A catamenial pad may be worn if desired to absorb the gel as it takes up moisture from the tissues and becomes less viscous. The user may, of course, use a douche after a suitable period of time to assure that a complete kill of sperm and microbes has been accomplished. A waiting period of 20 minutes to an hour is adequate for this purpose.

INDUSTRIAL APPLICATION

This invention finds application in health care industries and as a consumer product.

What is claimed is:

1. A virucidal, spermicidal vaginal gel consisting essentially of water, povidone and iodine wherein the weight ratio of povidone to iodine is at least 15 to 1 and wherein the povidone contains between 1 and 25 percent povidone having a molecular weight at least as low as 20 kd, said gel having a viscosity such that a conical body drawn from said gel does not visibly slump for a period of about one minute at 37 degrees celsius.

2. A virucidal, spermicidal vaginal gel consisting essentially of:
   a) a powder consisting essentially of a mixture, based on a total of 20 weight parts of 1), 2) and 3), of
      1) 10 parts by weight povidone iodine comprising about 85 percent by weight povidone having a molecular weight range of about 30 to about 50 kd, 10 percent iodide and 5 percent iodine;
      2) 5 parts by weight povidone having a molecular weight range of 30 to 50 kd;
      and 3) 5 parts by weight povidone having a molecular weight at least as low as 20 kd;
   to which b) sufficient water has been added to produce a gel having about 2.5 weight percent iodine based on the weight of the entire gel, said gel having a viscosity such that a conical body drawn from said gel does not visibly slump for a period of about one minute at 37 degrees celsius.

3. The gel of claim 1 or 2, wherein water is added to the gel in a closed container pressurized at between 1 and 3 atmospheres with pentane and mixing is conducted until the resulting mixture is saturated with pentane, sufficient water being added so that when the mixture is returned to atmospheric pressure it will spontaneously form a foam having a viscosity such that a conical body drawn from the foam does not visibly slump for a period of about one minute at 37 degrees celsius.

4. A method of preventing transmission of sexually transmitted diseases comprising the step of introducing to the vagina, prior to intercourse, a vaginal gel or foam consisting essentially of water, povidone and iodine wherein the weight ratio of povidone to iodine is at least 15 to 1 and wherein the povidone contains between 1 and 25 weight percent povidone having a molecular weight at least as low as 20 kd, said gel or foam having a viscosity such that a conical body drawn from the gel or foam does not visibly slump for a period of about one minute at 37 degrees celsius.

* * * * *